US00PP32241P2

(12) United States Plant Patent
Arts

(10) Patent No.: US PP32,241 P2
(45) Date of Patent: Sep. 29, 2020

(54) ***HYDRANGEA* PLANT NAMED 'H218913'**

(50) Latin Name: *Hydrangea macrophylla*
Varietal Denomination: H218913

(71) Applicant: HYDRANGEA BREEDERS ASSOCIATION B.V., De Kwakel (NL)

(72) Inventor: Niels Arts, Aalsmeer (NL)

(73) Assignee: Hydrangea Breeders Association B.V.

( * ) Notice: Subject to any disclaimer, the term of this patent is extended or adjusted under 35 U.S.C. 154(b) by 0 days.

(21) Appl. No.: 16/602,107

(22) Filed: Aug. 7, 2019

(51) Int. Cl.
*A01H 5/02* (2018.01)
*A01H 6/48* (2018.01)

(52) U.S. Cl.
USPC ..... Plt./250

(58) Field of Classification Search
USPC ..... Plt./226, 250
See application file for complete search history.

*Primary Examiner* — Susan McCormick Ewoldt
*Assistant Examiner* — Karen M Redden
(74) *Attorney, Agent, or Firm* — C. A. Whealy

(57) ABSTRACT

A new and distinct cultivar of *Hydrangea* plant named 'H218913', characterized by its upright and uniformly mounded plant habit; vigorous growth habit and rapid growth rate; freely branching habit with strong, thick and sturdy stems; freely and uniformly flowering habit; mophead-type inflorescences with numerous yellow green and light red purple-colored sterile flowers; and good postproduction longevity.

3 Drawing Sheets

Botanical designation: *Hydrangea macrophylla.*
Cultivar denomination: 'H218913'.

BACKGROUND OF THE INVENTION

The present invention relates to a new and distinct cultivar of *Hydrangea* plant, botanically known as *Hydrangea macrophylla*, commercially referred to as a mophead-type *Hydrangea* and hereinafter referred to by the name 'H218913'.

The new *Hydrangea* plant is a product of a planned breeding program conducted by the Inventor in De Kwakel, The Netherlands and Lengerich, Germany. The objective of the breeding program was to create new strong and freely-branching *Hydrangea* plants with strong sturdy stems, uniform flowering habit, large inflorescences with numerous showy sterile flowers, attractive sterile flower color and good postproduction longevity.

The new *Hydrangea* plant originated from a cross-pollination made by the Inventor in March, 2013 in De Kwakel, The Netherlands, of a proprietary selection of *Hydrangea macrophylla* identified as code number 05-0126-008, not patented, as the female, or seed, parent with *Hydrangea macrophylla* 'Noblesse', not patented, as the male, or pollen, parent. The new *Hydrangea* plant was discovered and selected by the Inventor as a single flowering plant from within the progeny of the stated cross-pollination in a controlled greenhouse environment in Lengerich, Germany in March, 2014.

Asexual reproduction of the new *Hydrangea* plant by vegetative tip cuttings in a controlled environment in De Kwakel, The Netherlands since April, 2015 has shown that the unique features of this new *Hydrangea* plant are stable and reproduced true to type in successive generations.

SUMMARY OF THE INVENTION

Plants of the new *Hydrangea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'H218913'. These characteristics in combination distinguish 'H218913' as a new and distinct *Hydrangea* plant:

1. Upright and uniformly mounded plant habit.
2. Vigorous growth habit and rapid growth rate.
3. Freely branching habit with strong, thick and sturdy stems.
4. Freely and uniformly flowering habit.
5. Mophead-type inflorescences with numerous yellow green and light red purple-colored sterile flowers.
6. Good postproduction longevity.

Plants of the new *Hydrangea* can be compared to plants of the female parent selection. Plants of the new *Hydrangea* differ primarily from plants of the female parent selection in sterile flower color as plants of the new *Hydrangea* have lighter red purple and yellow green-colored sterile flowers than plants of the female parent selection.

Plants of the new *Hydrangea* can be compared to plants of the male parent, 'Noblesse'. Plants of the new *Hydrangea* differ primarily from plants of 'Noblesse' in sterile flower color as plants of the new *Hydrangea* have yellow green and light red purple-colored sterile flowers whereas plants of 'Noblesse' have greenish white and purple-colored sterile flowers.

Plants of the new *Hydrangea* can be compared to plants of the *Hydrangea macrophylla* 'HBA215910', disclosed in U.S. Plant Pat. No. 29,171. In side-by-side comparisons, plants of the new *Hydrangea* differ primarily from plants of 'HBA215910' in the following characteristics:

1. Plants of the new *Hydrangea* are more freely branching than plants of 'HBA215910'.

2. Plants of the new *Hydrangea* have taller panicles than plants of 'HBA215910'.
3. Sepals of sterile flowers of plants of the new *Hydrangea* are more serrate to serrulate than sepals of sterile flowers of plants of 'HBA215910'.
4. Plants of the new *Hydrangea* have yellow green and light red purple-colored sterile flowers whereas plants of 'HBA215910' have dark red purple-colored sterile flowers with green-colored sectors.
5. Plants of the new *Hydrangea* and 'HBA215910' differ in reaction to aluminum sulfate treatment as sterile flower sepals of plants of the new *Hydrangea* treated with aluminum sulfate become yellow green and violet in color whereas sterile flower sepals of plants of 'HBA215910' treated with aluminum sulfate become light purple violet in color with greyed red-colored sectors.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet is a side perspective view of a typical flowering plant of 'H218913'.

The photograph on the second sheet is a close-up view of a typical inflorescence of 'H218913'.

The photograph on the third sheet is a top perspective view of a typical flowering plant of 'H218913' that has been "blued" (left) that is, treated with aluminum sulfate, and a top perspective view of a typical flowering plant of 'H218913' that has not been "blued" (right) that is, not treated with aluminum sulfate.

DETAILED BOTANICAL DESCRIPTION

Plants used in the aforementioned photographs and in the following description were grown during the late spring and early summer in 13-cm containers in a glass-covered greenhouse in De Kwakel, The Netherlands and under cultural practices typical of commercial *Hydrangea* production. During the production of the plants, day and night temperatures averaged 17° C. Plants of the new *Hydrangea* were one year old when the photographs and description were taken. Plants of the new *Hydrangea* can be successfully treated with aluminum sulfate to "blue" the inflorescences. In the following description, color references are made to The Royal Horticultural Society Colour Chart, 2015 Edition, except where general terms of ordinary dictionary significance are used.

Botanical description: *Hydrangea macrophylla* 'H218913'.

Parentage:

*Female, or seed, parent.*—Proprietary selection of *Hydrangea macrophylla* identified as code number 05-0126-008, not patented.

*Male, or pollen, parent.*—*Hydrangea macrophylla* 'Noblesse', not patented.

Propagation:

*Type cutting.*—By vegetative tip cuttings.

*Time to initiate roots, summer.*—About two weeks at temperatures about 23° C.

*Time to initiate roots, winter.*—About 18 days at temperatures about 20° C.

*Time to produce a rooted young plant, summer.*—About four weeks at temperatures about 23° C.

*Time to produce a rooted young plant, winter.*—About five weeks at temperatures about 20° C.

*Root description.*—Thick; typically whitish brown in color, actual color of the roots is dependent on substrate composition, water quality, fertilizer type and formulation, substrate temperature and physiological age of roots.

*Rooting habit.*—Freely branching; dense.

Plant description:

*Plant and growth habit.*—Upright and uniformly mounded plant habit; strong and sturdy stems; rapid growth rate and vigorous growth habit.

*Plant height.*—About 25 cm to 30 cm.

*Plant diameter or area of spread.*—About 45 cm to 50 cm.

Lateral branch description:

*Branching habit.*—Freely branching habit; when pinched, about eleven lateral branches develop per plant.

*Length.*—About 20 cm.

*Diameter.*—About 6 mm.

*Internode length.*—About 3 cm to 5 cm.

*Texture.*—Smooth, glabrous; fully developed, woody.

*Aspect.*—Upright to about 20° from vertical.

*Strength.*—Strong, sturdy.

*Color.*—When developing: Close to 146C; at internodes, close to 187A; lenticels, close to 187A. Developed: Close to 146C; at the internodes, close to 187A; when woody, close to 177D; lenticels, close to 187A.

Leaf description:

*Arrangement.*—Opposite, simple.

*Length.*—About 10 cm to 12 cm.

*Width.*—About 6 cm to 8 cm.

*Shape.*—Ovate.

*Apex.*—Acuminate to cuspidate.

*Base.*—Obtuse.

*Margin.*—Dentate to serrate.

*Texture, upper and lower surfaces.*—Rugose, glabrous.

*Venation pattern.*—Pinnate.

*Color.*—Developing and fully expanded leaves, upper surface: Close to NN137B; venation, close to 145B. Developing and fully expanded leaves, lower surface: Close to 138B; venation, close to 145C.

*Petioles.*—Length: About 3 cm to 4 cm. Diameter: About 3 mm. Texture, upper and lower surfaces: Smooth, glabrous. Color, upper surface: Close to 145B. Color, lower surface: Close to 145C.

Flower description:

*Flower type and habit.*—Showy sterile flowers and small inconspicuous fertile flowers arranged on mophead-type terminal panicles; panicles globular in shape; flowers face upright to outwardly depending on their position in the inflorescence.

*Fragrance.*—None detected.

*Natural flowering season.*—Plants begin flowering about one year after planting; flowering begins in the early summer and is continuous throughout the summer in Northern Europe.

*Flower longevity*.—Fertile flowers last about one month on the plant, fertile flowers not persistent; sterile flowers last about four months on the plant, sterile flowers persistent.

*Quantity of flowers*.—Freely flowering habit; about 25 fertile flowers per panicle and about 90 sterile flowers per panicle.

*Panicle height*.—About 8 cm to 10 cm.

*Panicle diameter*.—About 18 cm to 20 cm.

*Fertile flower buds*.—Length: About 3 mm. Diameter: About 3 mm. Shape: Flattened globular. Color: Close to 144D.

*Sterile flower buds*.—Length: About 3 mm. Diameter: About 3 mm. Shape: Flattened globular. Color: Close to 73B.

*Fertile flower diameter*.—About 6 mm.

*Fertile flower depth* (*height*).—About 5 mm.

*Sterile flower diameter*.—About 4.5 cm.

*Sterile flower depth* (*height*).—About 1 cm.

*Petals, fertile flowers*.—Quantity and arrangement: Four in a single whorl. Length: About 3.5 mm. Width: About 2 mm. Shape: Ovate. Apex: Acute. Base: Obtuse. Margin: Entire. Texture, upper and lower surfaces: Smooth, glabrous. Color: When opening, upper and lower surfaces: Close to 145A. Fully opened, upper and lower surfaces: Close to 144B, 145B and 62C; color does not change with development.

*Petals, sterile flowers*.—Quantity and arrangement: Four in a single whorl. Length: About 3 mm. Width: About 2 mm. Shape: Ovate. Apex: Acute. Base: Attenuate. Margin: Entire. Texture, upper and lower surfaces: Smooth, glabrous. Color: When opening, upper and lower surfaces: Close to N88C. Fully opened, upper surface: Close to N74C; color does not change with development. Fully opened, lower surface: Close to N74D; color does not change with development.

*Sepals, fertile flowers*.—Quantity and arrangement: Five in a single whorl. Length: About 2 mm. Width: About 2 mm. Shape: Ovate. Apex: Acute. Base: Obtuse. Margin: Entire. Texture, upper and lower surfaces: Smooth, glabrous. Color: When opening and fully opened, upper surface: Close to 145A; color does not change with development. When opening and fully opened, lower surface: Close to 145C; color does not change with development.

*Sepals, sterile flowers*.—Quantity and arrangement: Four in a single whorl. Length: About 2 cm. Width: About 2 cm to 2.5 cm. Shape: Deltoid. Apex: Acute to cuspidate. Base: Obtuse. Margin: Serrate to serrulate. Texture, upper surface: Smooth, glabrous. Texture, lower surface: Rugose, glabrous. Color: When opening, upper surface: Close to 144C. When opening, lower surface: Close to 144D. Fully opened, upper surface: Distally, close to 144B and proximally, close to 68A; with development, color becoming closer to 144A with edges, close to 181A; when "blued", distally becoming closer to 145A and proximally becoming closer to N87A. Fully opened, lower surface: Distally, close to 147D and proximally, close to 73B; with development, colors becoming closer to 144B and 181B, respectfully.

*Pedicels, fertile flowers*.—Length: About 1 cm. Diameter: About 1 mm. Strength: Moderately strong. Aspect: Mostly upright. Texture: Smooth, glabrous. Color: Close to 63D.

*Pedicels, sterile flowers*.—Length: About 2 cm to 3 cm. Diameter: About 1.5 mm. Strength: Strong. Aspect: Erect to about 45° from vertical. Texture: Smooth, glabrous. Color: Close to 63B.

*Reproductive organs, fertile flowers*.—Stamens: Quantity per flower: Eight. Filament length: About 1 mm. Filament color: Close to 75C. Anther length: About 1 mm. Anther shape: Conical. Anther color: Close to 75B. Pollen amount: Abundant. Pollen color: Close to NN155D. Pistils: Pistil quantity per flower: Three. Pistil length: About 1 mm. Stigma shape: Oval. Stigma color: Close to 75B and 186C. Style length: About 1 mm. Style color: Close to 75C. Ovary color: Close to 75C.

*Reproductive organs, sterile flowers*.—Stamens: Quantity per flower: About five to eight. Filament length: About 1 mm. Filament color: Close to 75C. Anther length: About 1 mm. Anther shape: Conical. Anther color: Close to 75B. Pollen amount: Abundant. Pollen color: Close to NN155D. Pistils: Pistil quantity per flower: Three. Pistil length: About 1 mm. Stigma shape: Oval. Stigma color: Close to 75B and 186C. Style length: About 1 mm. Style color: Close to 75C. Ovary color: Close to 75C.

*Seeds, only produced by fertile flowers*.—Quantity per fertile flower: About 20 to 30. Length: About 0.5 mm. Diameter: About 0.1 mm. Color: Close to 200C.

Pathogen & pest resistance: Under commercial production conditions, plants of the new *Hydrangea* have not been observed to be resistant to pathogens and pests common to *Hydrangea* plants to date.

Temperature tolerance: Plants of the new *Hydrangea* have been shown to be tolerant to temperatures ranging from about 3° C. to about 38° C.

It is claimed:

1. A new and distinct *Hydrangea* plant named 'H218913' as illustrated and described.

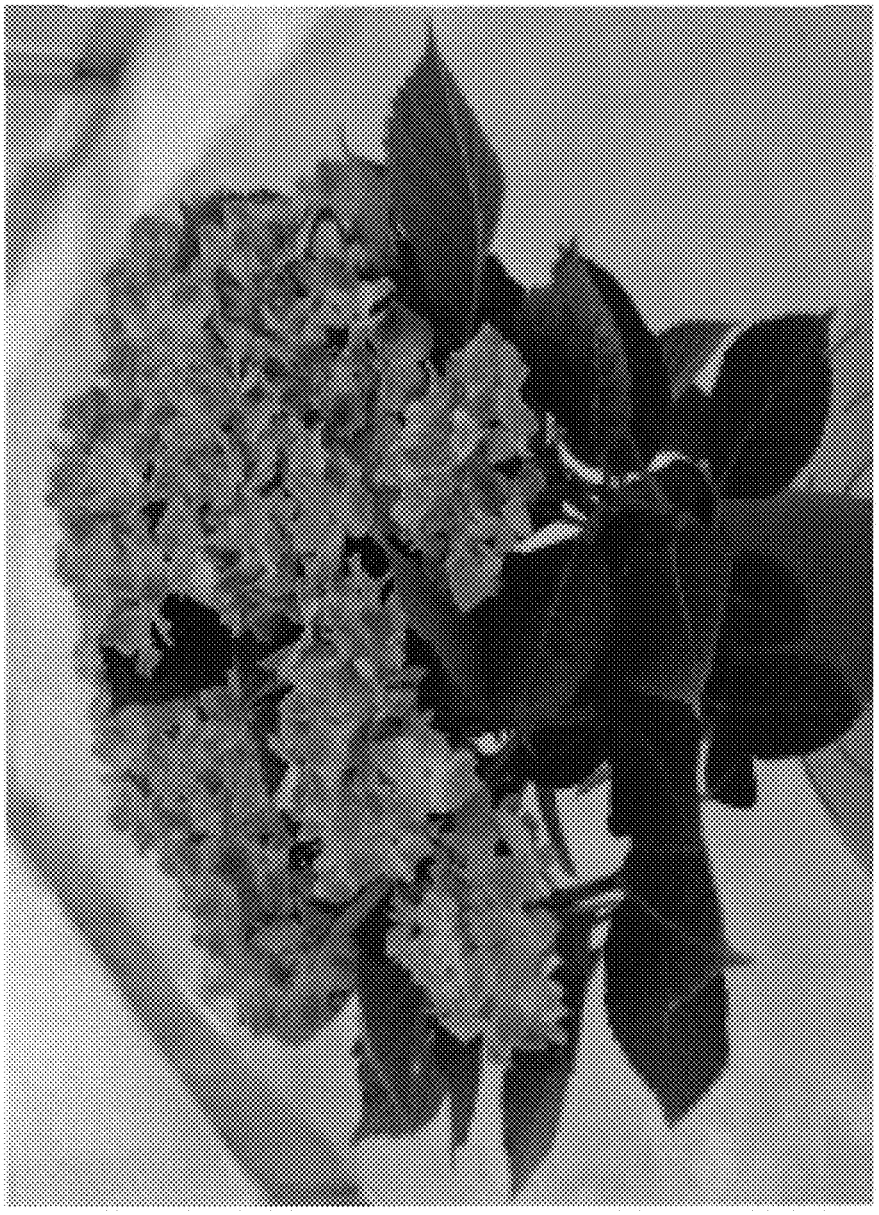

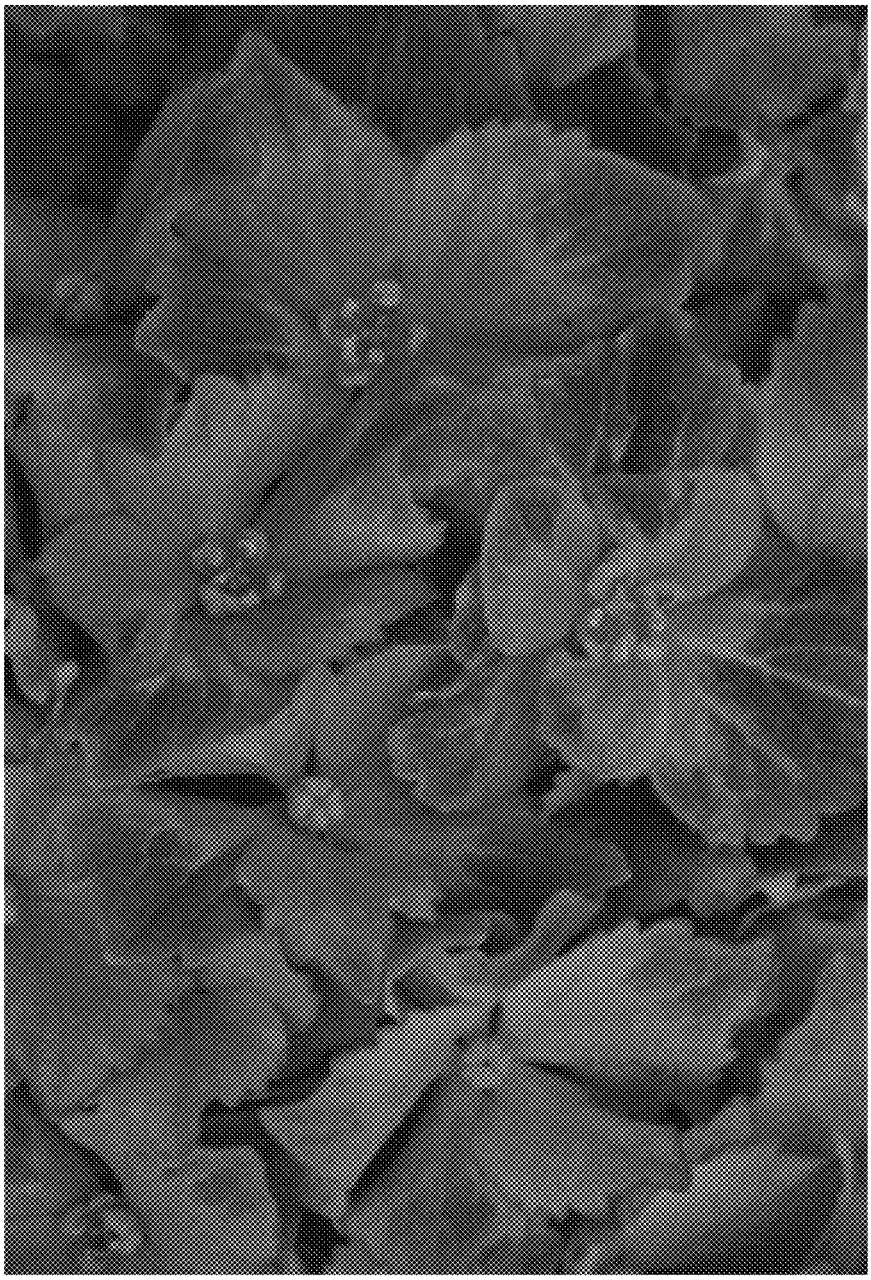

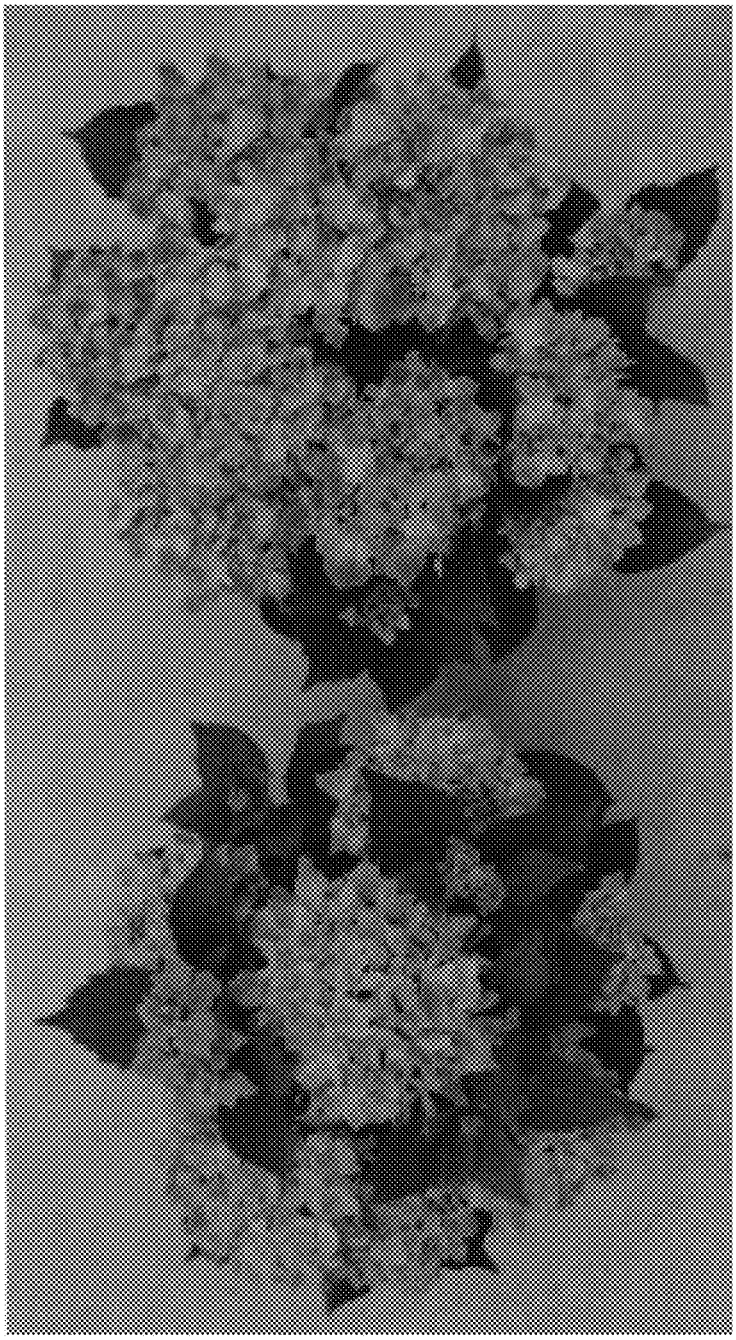

* * * * *